United States Patent [19]

McCombs

[11] 4,014,835

[45] Mar. 29, 1977

[54] COMPOSITION COMPRISING A BLEND OF A RESORCINOL-ALDEHYDE RESIN; AN ELASTOMER AND AN ORGANO SILICON COUPLING SYSTEM

[75] Inventor: Frank Paul McCombs, Granville, Ohio

[73] Assignee: Owens-Corning Fiberglas Corporation, Toledo, Ohio

[22] Filed: Apr. 14, 1975

[21] Appl. No.: 567,660

Related U.S. Application Data

[62] Division of Ser. No. 354,980, April 27, 1973, Pat. No. 3,900,661.

[52] U.S. Cl. .............................. 260/29.3; 260/25; 260/3; 260/28.5 A; 260/28.5 B; 260/42.15; 260/846; 260/847; 428/378; 428/392; 428/436
[51] Int. Cl.$^2$ ........................................ C08G 51/24
[58] Field of Search .............. 260/29.3, 28.5, 826, 260/844, 846, 25; 428/250

[56] References Cited

UNITED STATES PATENTS

| | | | |
|---|---|---|---|
| 3,424,608 | 1/1969 | Marzocchi et al. | 260/29.3 |
| 3,567,671 | 3/1971 | Janetos et al. | 260/28.5 |
| 3,702,798 | 11/1972 | Shannon | 260/29.3 |
| 3,850,866 | 11/1974 | Uffner | 260/29.3 |

OTHER PUBLICATIONS

H. Bennett, The Chemical Formulary, vol. XIV, Chemical Publishing Co., New York, 1968, pp. 248 & 249.

*Primary Examiner*—Theodore E. Pertilla
*Attorney, Agent, or Firm*—John W. Overman; Keith V. Rockey; Philip R. Cloutier

[57] ABSTRACT

A composition for use in the treatment of glass fibers and glass fibers treated with same for use as reinforcement for elastomeric materials in the manufacture of glass fiber reinforced elastomeric products comprising a blend of a resorcinol-aldehyde resin and an elastomer and a coupling system comprising an amino-substituted organo silicon compound and an organo silicon compound containing at least one beta-haloalkoxy group.

26 Claims, No Drawings

COMPOSITION COMPRISING A BLEND OF A RESORCINOL-ALDEHYDE RESIN; AN ELASTOMER AND AN ORGANO SILICON COUPLING SYSTEM

The present application is a division of application Ser. No. 354,980, filed Apr. 27, 1973, and now Pat. No. 3,900,661.

BACKGROUND OF INVENTION

This invention relates to glass fiber-elastomeric products, and more particularly to the treatment of glass fibers and compositions in the treatment of glass to facilitate the combination of glass fibers with elastomeric materials such as in the manufacture of glass fiber-reinforced elastomeric products.

The term "glass fibers," as used herein, is intended to refer to and include (1) continuous fibers formed by rapid attenuation of hundreds of streams of molten glass and to strands formed when such continuous glass fiber filaments are gathered together as they are being formed; and to yarns and cords formed by plying and/or twisting a number of strands together, and to woven and non-woven fabrics which are formed of such glass fiber strands, yarns or cords, and (2) discontinuous fibers formed by high pressure steam, air or other suitable attenuating force directed onto multiple streams of molten glass issuing from a glass melting bushing or from an orifice containing spinner, and to yarns that are formed when such discontinuous fibers are gathered together to form a sliver which is drafted into a yarn; and to woven and nonwoven fabrics formed of such yarns of discontinuous fibers, and (3) combinations of such continuous and discontinuous fibers in strands, yarns, cords and fabrics formed thereof.

As used herein, the term "elastomer" is intended to mean and include natural rubber in the cured or uncured stage, vulcanized or unvulcanized stage, and synthetic organic elastomeric materials such as nitriles, acrylics and esters and terpolymers thereof with styrene and acrylontriles, styrene and vinyl pyridine; and EPDM rubbers as represented by butadiene polymers and copolymers with monoolefins such as butadiene-styrene vinyl pyridine terpolymers, chloroprene, isoprene, neoprene, isobutyl rubber and the like elastomeric polymers and copolymers in their cured or uncured stages, and vulcanized or unvulcanized stages. Included also are the EPDM rubbers, such as formed by the interpolymerization of ethylene, an alpha-monoolefin having from 3–20 carbon atoms, such as propylene, and polyene, such as dicyclopentadiene, 1,4-hexadiene and preferably an alkylene or alkylidene norbornene, such as 5-alkylidene-2-norbornene and the like in which the alkylidene group numbers from 2–12 carbon atoms, and polysulfone rubbers.

It is now well known to combine glass fibers with elastomeric matrials in the manufacture of glass fiber reinforced elastomeric products, such as driving belts, timing belts, pneumatic tires, etc. One of the problems which has been encountered in such combinations of glass fibers with elastomeric products is the problem of securely anchoring the glass fiber surfaces to the elastomeric material in which the glass fibers are distributed. It is believed that this problem stems in part from the fact that the glass fibers are completely smooth, rod-like members and in part from the fact that the glass fiber surfaces are highly hydrophilic in nature, thereby resulting in the formation of a thin but tenacious film of water on the glass fiber surfaces which serves to destroy any bond, chemical or physical, which would otherwise be formed between the glass fiber surfaces and the elastomeric material with which the glass fibers are combined.

To minimize the problems of bonding the glass fiber surfaces to the elastomeric materials, it has been the practice in the manufacture of glass fiber-reinforced elastomeric products to make use of glass fibers in the form of individual glass fibers having a coating on the surfaces thereof to intertie the individual glass fibers to the elastomeric material in which the glass fibers are distributed, or preferably glass fibers in the form of yarns, cords, chopped strands or fabrics, hereinafter referred to as bundles, containing an impregnant therein which also serves to intertie the glass fiber bundles to the elastomeric material in which the bundles are distributed.

Various compositions may be used in the treatment of glass fibers, either as size compositions for application to the surfaces of individual glass fibers, or as impregnant compositions for impregnation of glass fiber bundles. Conventional size compositions are illustrated in U.S. Pat. No. 3,424,608 and are generally formed of a film-forming material, a wetting agent and a glass fiber lubricant. Most size compositions now in use are formulated to contain a glass fiber anchoring agent, preferably in the form of an organo silane, such as gamma-aminopropyltriethoxy silane or a Werner complex compound.

Impregnating compositions now in use are formulated to contain a resorcinol-aldehyde resin component and an elastomer component. Impregnating compositions are illustrated in U.S. Pat. Nos. 3,424,608 and 3,567,671, as well as numerous others. It has been the practice in the manufacture of glass fiber reinforced elastomeric products to first coat the individual glass fiber filaments with a size compositon embodying an organo silicon compound as an anchoring agent, and then impregnate a bundle of the sized fibers with an impregnating composition formulated of a resorcinol-aldehyde resin component and an elastomer component. The resulting bundle can then be combined with an elastomeric material in the manufacture of glass fiber-reinforced elastomeric products.

The size coating on the individual glass fibers is believed to improve the processing characteristics of the glass fibers without destroying their fibrous characteristics and to promote the bonding relationship between the elastomeric component of the impregnant. The impregnant is believed to intertie the impregnated bundle with the elastomeric material constituting the continuous phase with which the bundles are combined.

It has been proposed to modify the above described practice by eliminating one step of the sizing and impregnating technique. Such proposals most frequently suggest that the impregnating composition be applied directly to the individual glass fibers, preferably as they are formed, to form a coating thereon. However, it has been found that the bonding relationship between glass fibers treated in this manner and elastomeric materials is poor unless the impregnating composition is formulated to contain an organo silicon compound as an anchoring agent.

Such anchoring agents can be formulated with impregnating compositions of the type described above. However, the resulting composition is not completely stable because the highly acidic nature of the organo silicon compounds tends to cause coagulation of the latex containing the resorcinol-aldehyde resin and the elastomer.

It is therefore an object of the present invention to provide a composition for use in the treatment of glass fibers which contains a resorcinol-aldehyde resin component and an elastomer component which overcomes the foregoing disadvantages.

It is a more specific object of the present invention to provide a composition for use in the treatment of glass fibers to improve the bonding relationship between glass fibers and elastomeric materials in the manufacture of glass fiber reinforced elastomeric products in which a system of organo silicon compounds is formulated with a latex of a resorcinol-aldehyde resin and an elastomer without resulting in coagulation of the latex.

DESCRIPTION OF THE PREFERRED EMBODIMENTS

The concepts of this invention reside in a composition for use in the treatment of glass fibers in which a latex containing a resorcinol-aldehyde resin and an elastomer is formulated to include an organo silicon compound containing at least one organic group attached directly to the silicon which is substituted with at least one amino group and at least one organo silicon compound containing at least one beta-haloalkoxy group

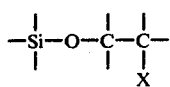 (1)

wherein X is halogen.

Without limiting the present invention as to theory, it is believed that the beta-haloalkoxy group referred to above, which is significantly more resistant to hydrolysis in aqueous media as compared to organo silicon compounds containing a simple alkoxy group, stabilizes the amino substituted organo silicon in the alkaline latex composition to prevent or substantially minimize coagulation of the latex and thereby assure stability in the resulting composition. In addition, the organo silicon compounds containing the beta-haloalkoxy group contribute to the improved bonding relationship between the glass fibers and the elastomer component of the impregnant.

The resulting composition can be applied to the individual glass fibers to form a coating on the surfaces thereof, or to a bundle of sized or unsized glass fibers as an impregnant, to improve the bonding relationship between the glass fibers and an elastomeric material with which the treated glass fibers are combined in the manufacture of glass fiber-reinforced elastomeric products.

As the amino-substituted organo silicon compound, use is preferably made of at least one silane containing 1 to 3 readily hydrolyzable groups and containing at least one organic group attached directly to the silicon atom, with at least one of the organic groups being substituted by at least one amino group. Any remaining valences on the silicon atom are taken up by hydrogen. Such silanes are hydrolyzable in aqueous media and, thus, use can also be made of the corresponding hydrolysis products of such silanes, specifically the corresponding silanols and siloxanes.

It is frequently advantageous to first hydrolyze the silane with aqueous media prior to formulating the composition of this invention. Such hydrolysis is preferably effected by simply contacting the silane with water or an aqueous alkaline solution containing an emulsifying agent to facilitate dispersion of the silane.

The silanes most preferred for use in the practice of this invention are themselves well known to the art, and include silanes having the formula

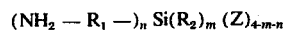 2 wherein $R_1$ is a divalent organic group containing 2 to 10 carbon atoms, such as alkylene (i.e., dimethylene, trimethylene, tetramethylene, pentamethylene, etc.), alkenylene (i.e. ethenylene, propenylene, etc.), cycloalkylene (i.e., cyclopentylene, cyclohexylene, etc.) or arylene (i.e., phenylene, etc.); $R_2$ is an organic group and preferably a hydrocarbon group containing 1 to 6 carbon atoms including alkyl (i.e. methyl, ethyl, isopropyl, etc.), alkenyl (i.e., vinyl, allyl, etc.), cycloalkyl containing 4 to 6 carbon atoms (i.e., cyclopentyl, cyclohexyl, etc.) or phenyl, including the hydroxy, epoxy or mercapto derivatives thereof; Z is a readily hydrolyzable group, such as halogen (chlorine or bromine) or a $C_1$ to $C_4$ alkoxy group (i.e., methoxy, ethoxy, propoxy, etc.); $n$ is an integer from 1 to 3 and $m$ is 0 or 1. Also suitable for use in this invention are the hydrolysis products thereof.

Illustrative of such silanes include the following:
gamma-aminopropyltrimethoxysilane
delta-aminobutyltriethoxysilane
p-aminophenyltriethoxysilane
3-aminocyclohexyltrimethoxysilane
beta-aminovinyltrimethoxysilane
gamma-aminoallyltrimethoxysilane
bis-(gamma-aminopropyl)diethoxysilane
beta-aminoethylmethyldiethoxysilane
gamma-aminopropylallyldiethoxysilane
and the corresponding hydrolysis products thereof including the silanols and siloxanes of each of the foregoing silanes.

Also suitable for use in the practice of this invention are polyamino silanes; these silanes have the general formula

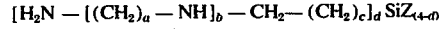 3 wherein $a$ is an integer from 1 to 3, $b$ is an integer from 1 to 3, $c$ is an integer from 1 to 3, $d$ is 1 to 2, and Z is as described above.

Such silanes include the following:
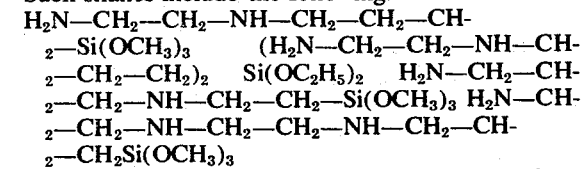

and the corresponding hydrolysis products thereof.

Another amino silicon compound which can advantageously be used in the practice of the invention is the polyamino-functional silane marketed by Dow Corning, first under the trademark XZ-2-2287 and now under the trademark Z-6050. The polyamino silane is prepared by reaction of the compounds

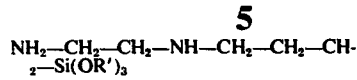
(4)

wherein R' is $C_1$ to $C_4$ alkyl (e.g. methyl, ethyl, propyl, etc.) with ethylene imine

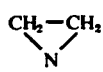
(5)

to form the compounds represented by the following:

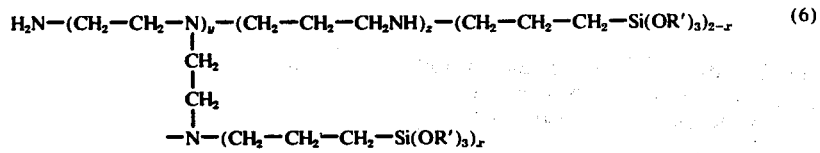
(6)

wherein $x$ is 0 or an integer from 1 to 2 and $y$ and $z$ are integers.

The commercially available form is the material where R' is methyl, although it will be understood that the other alkoxy derivatives can be prepared in a like manner. In general, use is made from 1 to 10 moles of the imine per mole of diamino starting material.

The organo silicon compounds containing the beta-haloalkoxy groups as described above are described in detail in copending applications Ser. No. 347,264, filed Apr. 2, 1973 and Ser. No. 347,241, filed Apr. 2, 1973 both of which are assigned to the assignee of this invention. As described in the foregoing copending application Ser. No. 347,264, the compounds are prepared by reaction of a halosilane

7 wherein $R_3$ is an organic group, and preferably alkyl (i.e., methyl, ethyl, propyl, etc.), alkenyl (i.e., vinyl, allyl, butenyl, etc.), cycloalkyl (i.e., cyclopentyl, cyclohexyl, etc.), aryl such as phenyl as well as substituted derivatives thereof; $e$ is 0 or an integer from 1 to 2; and X is halogen and preferably chlorine or bromine, with an alkylene oxide containing 1 to 6 carbon atoms

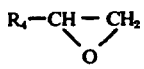
(8)

wherein $R_4$ is $C_1$ to $C_4$ alkyl or hydrogen and either (1) a monoepoxide in the form of styrene oxide or a monoepoxide of the formula

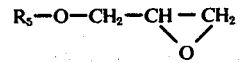
(9)

wherein $R_5$ is an aryl group and preferably phenyl or phenyl substituted with an amino group, a halogen group, an alkyl group; alkyl containing 1 to 20 carbon atoms and substituted derivatives thereof; an alkenyl group containing 2 to 8 carbon atoms (e.g., vinyl, allyl, etc.); a group having the formula

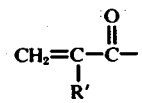
(10)

wherein R' is hydrogen or methyl; (2) a diepoxide having the formula

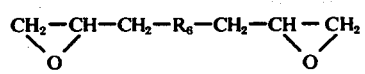
(11)

wherein $R_6$ is a divalent organic radical such as oxyalkyleneoxy containing 1 to 10 carbon atoms; oxyalkyleneoxyalkyleneoxy containing 2 to 20 carbon atoms, divalent aromatic groups such as a group of the formula

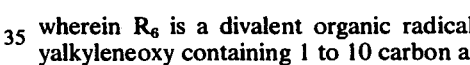
(12)

or

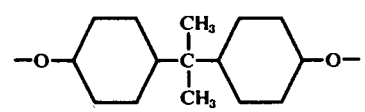
(13)

or (3) a cycloalkane diepoxide including the following compounds:

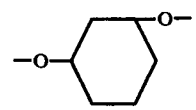
(14)

(RD 4 or ERL 4206)

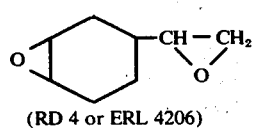
(15)

(ERR 4205)

-continued (16)

[Structure: epoxycyclohexane-CH₂-O-C(=O)-(CH₂)₄-C(=O)-O-CH₂-epoxycyclohexane with CH₃ groups]
(ERR 4289)

(17)

[Structure: epoxycyclohexane-C(=O)-O-CH₂-epoxycyclohexane]
(ERR 4221)

Illustrative of such monoepoxides are phenyl glycidyl ether, cresyl glycidyl ether, allyl glycidyl ether, glycidyl acrylate, glycidyl methacrylate, a mixture of n-octyl and n-decyl glycidyl ethers (Epoxide No. 7 from Procter and Gamble) and a mixture of n-dodecyl and n-tetradecyl glycidyl ethers (Epoxide No. 8 from Procter and Gamble).

A number of such diepoxides are commercially available from Dow and Ciba and include the following:

$$C30\ 2-CH-CH_2-O-(CH_2)_4-O-CH_2-CH-2$$
 with epoxide rings
(RD 2)

$$CH_2-CH-CH_2-O-(CH_2-CH_2-O)_{1.5\sim}-CH_2-CH-CH_2$$ (19)
with epoxide rings
(DER 736)

$$CH_2-CH-CH_2-O-(CH_2-CH_2-O)_{4.31}-CH_2-CH-CH_2$$ (20)
with epoxide rings
(DER 732)

$$CH_2-CH-CH_2-O-(CH_2-CH_2-O)_{4.5\sim}-CH_2-CH-CH_2$$ (21)
with epoxide rings
(DER 508)

[Structure: CH₂-CH(O)-CH₂-O-C₆H₄-C(CH₃)₂-C₆H₄-O-CH₂-CH(O)-CH₂] (22)
(DER 332)

[Structure: CH₂-CH(O)-CH₂-O-C₆H₁₀-O-CH₂-CH(O)-CH₂] (23)
(ERE 1369)

In the preparation of such compounds, use is generally made of 1 to 3 epoxide equivalents of the alkylene oxide and 0.5 to 3 epoxide equivalents of the mono- or diepoxides described above. Where the epoxide employed is a diepoxide, it is generally preferred that the total of e plus the epoxide equivalents of the alkylene oxide total at least 2.1 and preferably at least 2.5 to minimize gel formation.

The resulting reaction product is most frequently a mixture of compounds which is preferably used as such without separation of individual compounds thereof; however, it will be understood that the predominant compounds contained in the reaction mixture can be separated and utilized in the practice of this invention. Specific compounds prepared can be illustrated by way of the following:

$$SiX_4 + R_4-CH-CH_2 + R_5-O-CH_2-CH-CH_2 \longrightarrow$$
with epoxide rings $$Si\left(-O-CH_2-CH-R_4\atop X\right)_f \left(O-CH_2-CH-CH_2-O-R_5\atop X\right)_g$$ (24)

(8)

wherein $f$ and $g$ are each integers from 1 to 3; or $$SiX_4 + R_4-CH-CH_2 + \text{[cyclohexane]}-CH-CH_2 \longrightarrow$$
with epoxide rings -continued

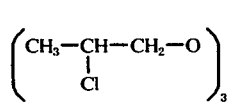
(25)

Where the epoxide is a diepoxide, the reaction product includes compounds containing no free epoxy group and/or compounds containing free epoxy groups; the reaction can be illustrated by the following:

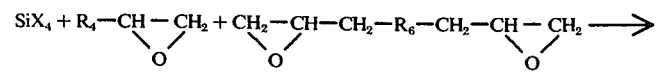

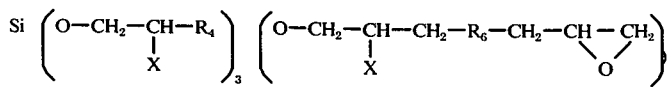

and/or (26)

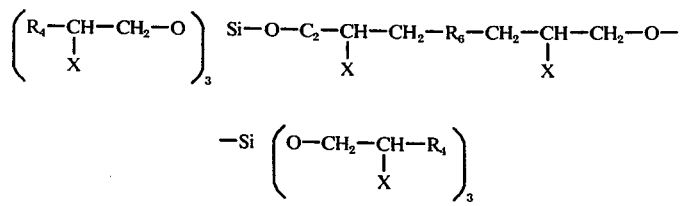

The preparation of compounds containing the free epoxy group is generally favored by employing 2 or more epoxide equivalents of the diepoxides. As will be appreciated by those skilled in the art and as is described in the foregoing copending applications, analogous compounds are prepared where c is 1 or 2, with the valence of the beta-haloalkoxy groups being decreased correspondingly.

As is also described in the foregoing copending applications, the alkylene oxide can be replaced in whole or in part by a monohydric alcohol.

Organo silicon compounds preferred for use in the practice of this invention are those prepared using propylene oxide and DER 322, using 3 epoxide equivalents of the propylene oxide and 1 epoxide equivalent of the diepoxide. The product of this reaction is a mixture which contains the compound

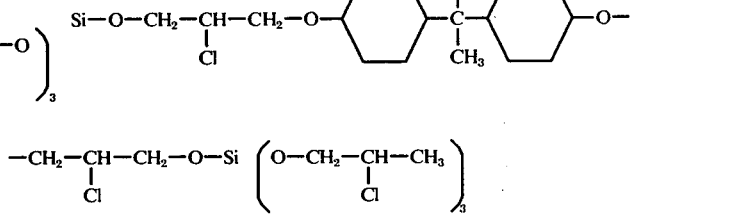
(27)

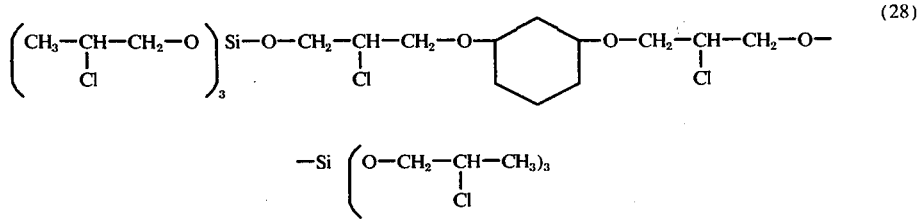

Another preferred reaction product is that prepared using 3 epoxide equivalents of propylene oxide and 1 epoxide equivalent of DER 1359; this reaction product includes the following compound:

(28)

The reaction mixtures described above are preferably used without separation of the above compounds, although them compounds themselves can likewise be employed.

Alternatively, use can also be made of the reaction product of the halosilane $(R_3)_e \, SiX_{(4-e)}$ (29)

with (1) either a styrene oxide or a monoepoxide

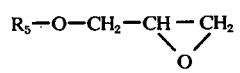
(30)

and (2) at least one of the diepoxides described above, as described in copending application Ser. No.

347,241. In this embodiment of the invention, the reaction product is preferably prepared using 1 to 3 epoxide equivalents of (1) and 0.5 to 3 epoxide equivalents of (2). If desired, a portion of the styrene oxide or monoepoxide (1) can be replaced by a monohydric alcohol and/or a lower alkylene oxide in amounts up to 2 moles of alcohol and/or alkylene oxide per mole of the halosilane.

The reaction product is generally in the form of a mixture of compounds, and it is generally preferred that the product be utilized as such. The reaction product contains compounds containing at least 2 beta-haloalkoxy groups, and the specific compounds produced can be illustrated by way of the following:

in the above equations can be replaced by $R_3$ groups, the residue of an alkylene oxide, andor the residue of the monohydric alcohol.

For further description of the foregoing beta-haloalkoxy compounds, reference can be made to the foregoing copending applications, the disclosures of which are incorporated herein by reference.

The relative proportions of the amino-substituted organo silicon compounds and the beta-haloalkoxy compounds are not critical, and can be varied within wide limits. It has been found that best results are usually obtained where the total of the amino-substituted organo silicon compound and the beta-haloalkoxy compound contains 1 to 35%, and preferably 5 to 30%

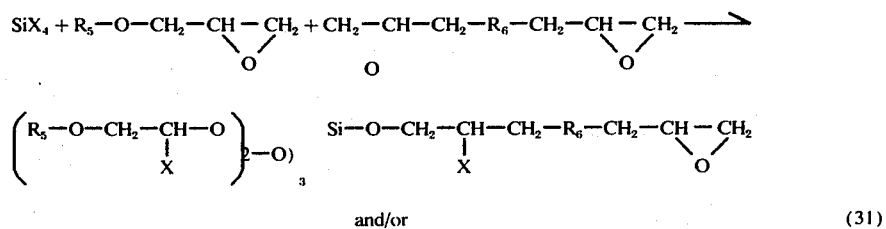

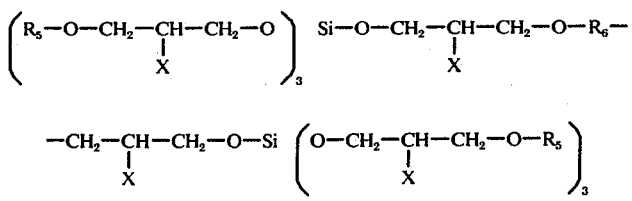 (31)

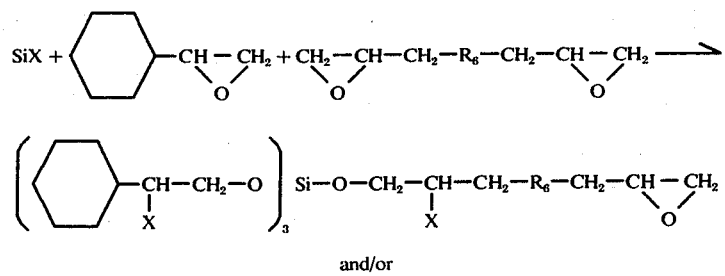

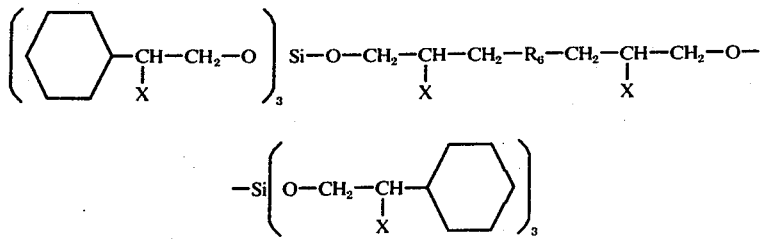 (32)

As indicated in the foregoing copending applications, up to 2 of the groups

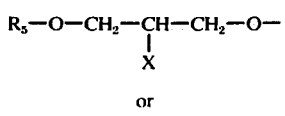

or

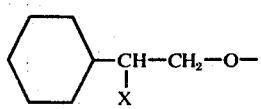

by weight of the amino-substituted organo silicon compound.

The amount of the silicon compounds employed with the blend of the elastomer and the resorcinol-aldehyde resin components is likewise not critical to the practice of the invention. It is generally sufficient that the total of the silicon-containing compounds constitute from 0.1 to 25%, and preferably 1 to 15% of the total solids of the treating composition.

The treating compositions with which the silicon compounds are formulated are generally well-known to those skilled in the art and are described in U.S. Pat. Nos. 3,391,052; 3,402,064; 3,424,608; 3,506,476;

3,533,830; 3,567,671; 3,591,357 as well as others. Such compositions are generally formulated to contain 1 to 10 parts by weight of a resorcinol-aldehyde resin component and 20 to 80 parts by weight of at least one elastomer on a solids basis. Some of such compositions are formulated to contain other polymeric components to provide treated glass fibers having the desired degree of stiffness and tackiness; such polymeric additives are fully described in the foregoing patents.

The treating composition formulated in accordance with the practice of the present invention is preferably applied to glass fibers as they are formed to form a thin coating of the solids of the composition along with the silicon compounds. In general, it is preferred that the composition be applied in an amount sufficient to provide a coating constituting 1 to 20% by weight of the glass fibers. Subsequent to coating, the glass fibers can be gathered together in a conventional manner to form strands, which in turn can be twisted and plied together to form cords, without the need of subsequent processing, for combination with elastomeric materials in the manufacture of glass fiber-reinforced elastomeric products.

Alternatively, the treating composition of this invention can be applied as an impregnating composition to bundles of glass fibers, which preferably but not necessarily have a thin film of coating of a glass fiber size on the individual surfaces. Tecniques for impregnation are now well known and are described in the foregoing patents; bundles of glass fibers are preferably immersed in a bath of the treating composition of the invention and subjected to a sharp bend while immersed therein to open the bundle and permit complete penetration of the composition into the bundle whereby the solids of the composition serve to separate the fibers each from the other and fill the interstices between the fiber filaments to define a unitary bundle structure. Impregnation is generally carried out to deposit from 5 to 30% dry solids in the glass fiber bundle.

Having described the basic concepts of the invention, reference is now made to the following examples which are provided by way of illustration, and not by way of limitation, of the practice of the invention in the formulation of the treating composition of the invention and its use in the treatment of glass fibers.

EXAMPLE 1

Using the procedure described in Example 1 of co-pending application Ser. No. 347,264, one mole of silicon tetrachloride is reacted with 0.5 mole (1 epoxide equivalent) of DER 332 and 3 moles of propylene oxide.

A sample of 80 g of the reaction product is then mixed with 50 g of an emulsifying agent RL 3773, which is an amphoteric sulfated oil from Procter Chemical. To the resulting mixture, there is added 20 g of gamma-aminopropyltriethoxy silane (A1100 from Union Carbide) in 100 g of deionized water. The resulting mixture is then blended with 2000 g of a glass fiber treating composition of the type described in U.S. Pat. No. 3,567,671.

The resulting composition contained the following:

|  | Parts by weight |
|---|---|
| Silicon compound mixture (plus emulsifier) | 150 |
| Resorcinol-formaldehyde resin (Penacolyte R2120 - 75% solids) | 48 |
| Vinyl pyridine-butadiene-styrene terpolymer (Gentac FS - General Tire and Rubber Co. 42% solids) | 900 |
| Vinyl chloride-vinylidene chloride copolymer (Dow latex 874 - 50% solids) | 350 |
| Microcrystalline paraffin wax (Vultex Wax no. 5 - 56% solids) | 200 |
| Water | 602 |

It is found that the treating composition is stable over long periods of time, and that there is no tendency for the latex components to coagulate and/or precipitate from the aqueous dispersion.

The above composition is employed in the impregnation of a bundle of previously sized glass fibers, and the impregnated bundle combined with rubber as in the manufacture of glass fiber-reinforced elastomeric products. Good adhesion between the impregnated bundle and the rubber is obtained.

EXAMPLE 2

Using the procedure described in Example 4 of Serial No. 347,264, 1 mole of SiCl$_4$ is reacted with 3 moles of propylene oxide and 0.5 mole (1 epoxide equivalent) of the epoxide DER 1359.

A sample of 83.3 g of the reaction product is mixed with 10 g of a emulsifier (CA 630 from GAF Corp. which is an octylphenoxypoly(ethyleneoxy)ethanol).

The resulting mixture is then blended with 16.7 g of gamma-aminopropyltriethoxy silane, and this mixture is blended with 2000 g of the composition employed in Example 1 to form the following composition:

|  | Parts by weight |
|---|---|
| Silicon compound mixture (plus emulsifier) | 110 |
| Resorcinol-formaldehyde resin (75% solids) | 48 |
| Vinyl pyridine-butadiene-styrene terpolymer (42% solids) | 900 |
| Vinyl chloride-vinylidene chloride copolymer (50% solids) | 350 |
| Microcrystalline paraffin wax (56% solids) | 200 |
| Water |  |

A bundle of glass fibers is subjected to impregnation with the final composition using the procedure described in Example 1. The resulting bundle in the form of a cord is subjected to analysis and found to have a loss on ignition (LOI) of 19.8% and a tensile strength of 72.3 lbs. A sample of the cord is also molded between the strips of rubber to determine the hot U adhesion value which is found to be 28.9 lbs.

EXAMPLE 3

Using the procedure described in Example 1, the adduct of SiCl$_4$, propylene oxide and DER 332 is prepared, and the resulting product is subjected to purification by chromatography to isolate the compound

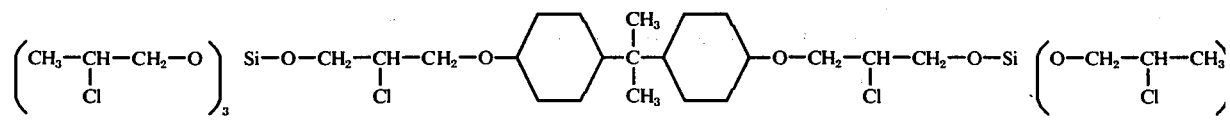

(33)

A sample of 80 g of the above compound is mixed with 50 g of the emulsifying agent RL 3773 and 20 g of gamma-aminopropyltrimethoxysilane in 100 g of water. The resulting mixture is then blended with a blend of a resorcinol-aldehyde resin and an elastomer to form the following composition:

| | Parts by weight |
|---|---|
| Silicon compound mixture (plus emulsifier) | 150 |
| Resorcinol-formaldehyde resin (75% solids) | 50 |
| Vinyl pyridine butadiene-styrene terpolymer (42% solids) | 800 |
| Water | 400 |

The above composition can be applied to individual glass fiber filaments, preferably as they are formed, to form a coating on the surfaces thereof, or as an impregnant.

EXAMPLE 4

A sample of 15 g of the polyamino functional silane Z-6050 in isopropanol is first hydrolyzed with water and then blended with a mixture of 60 g of the reaction product described in Example 1 above and 40 g of emulsifying agent RL 3773. The resulting mixture is then blended with 2000 g of a glass fiber treating composition of the type described in U.S. Pat. No. 3,567,671, except that the vinyl chloride-vinylidene chloride component is replaced by a dicarboxylated butadiene-styrene copolymer component to form the following:

| | Parts by weight |
|---|---|
| Silicon compound mixture (plus emulsifier) | 115 |
| Resorcinol-formaldehyde resin (75% solids) | 48 |
| Vinyl pyridine-butadiene-styrene terpolymer (42% solids) | 900 |
| Dicarboxylated butadiene-styrene copolymer (50% solids - Pliolite 4121 from Goodyear Tire and Rubber Co.) | 350 |
| Microcrystalline parafin wax (56% solids) | 200 |
| Water | 502 |

The dicarboxylated butadiene-styrene copolymer is, as indicated, marketed by Goodyear Tire and Rubber Co. and has been found to be markedly superior to the monocarboxylated copolymer described in the foregoing U.S. Pat. No. 3,567,671. Other dicarboxylated butadiene-styrene copolymers which can be used in lieu of the Pliolite 4121 include Pliolite 4264, Pliolite 4303, Pliolite 386, Pliolite 402 and Pliolite 388. These copolymers have a ratio of styrene to butadiene of at least 50/50, and generally within the range of 50/50 to 85/15, and are prepared by polymerization of butadiene and styrene in the presence of small amounts of a dicarboxylic acid containing ethylenic unsaturation, with less than 2% emulsifier.

The above composition can be applied to glass fiber filaments to form a coating on the individual surfaces thereof, or to bundles of glass fibers as an impregnant, to improve the bonding relationship between glass fibers and elastomeric materials in the manufacture of glass fiber reinforced elastomeric products.

EXAMPLE 5

Using the procedure described in Example 4, 20 g of the polyamino functional silane Z-6050 hydrolyzed with water is admixed with 80 g of the SiCl$_4$-epoxide reaction product described in Example 2 and 50 g of emulsifying agent RL 3773.

The resulting mixture is then combined with 2200 g of the treating composition described in Example 4 to form the following composition:

| | Parts by weight |
|---|---|
| Silicon compound mixture (plus emulsifier) | 150 |
| Resorcinol-formaldehyde resin (75% solids) | 50 |
| Vinyl pyridine-butadiene-styrene terpolymer (42% solids) | 900 |
| Dicarboxylated butadiene-styrene copolymer (50% solids - Pliolite 4121) | 350 |
| Microcrystalline paraffin wax (56% solids) | 200 |
| Water | |

General examples of the foregoing glass fiber treating compositions may be illustrated by way of the following example in which all but the mixture of the amino-substituted organo silicon compound and the beta-haloalkoxy silicon compounds are expressed on a solids basis:

| | Parts by weight solids |
|---|---|
| Silicon compound mixture | 4 – 35 |
| Resorcinol-aldehyde resin | 2 – 10 |
| Vinyl pyridine-butadiene-styrene terpolymer | 20 – 60 |
| Vinyl chloride-vinylidene chloride copolymer or dicarboxylated butadiene-styrene copolymer | 15 – 40 |
| Microcrystalline paraffin wax | 3 – 30 |

The balance of the foregoing is water which is present in an amount to adjust the solids content to within the desired range, usually from 10 to 50%, and preferably from 12 to 35%, solids by weight.

Additional examples of compositions which can be formulated in accordance with the concepts of the invention for application to glass fiber filaments to form a coating on the individual surfaces thereof, preferably as the filaments are formed, or as an impregnant for bundles of glass fibers, are illustrated by way of the following examples:

EXAMPLE 7

Using the procedure described in Example 2, the SiCl$_4$-epoxide described therein is prepared and subjected to purification to separate as the major constituent the following compound:

(34)

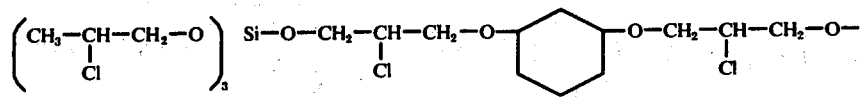

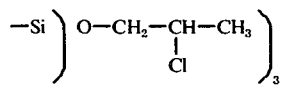

This compound is then admixed with delta-aminobutyl-trimethoxysilane which has been hydrolyzed with water. The resulting mixture is then formulated with a composition of the type described above in Example 5 as follows:

| | Parts by weight solids |
|---|---|
| Silicon compound mixture | 6 |
| Resorcinol-formaldehyde resin | 5 |
| Vinyl pyridine-butadiene-styrene terpolymer | 35 |
| Dicarboxylated butadiene-styrene copolymer | 25 |
| Microcrystalline paraffin wax | 5 |

EXAMPLE 8

Twenty grams of N-(beta-aminoethyl)gamma-aminopropyltrimethoxy silane is hydrolyzed with water and blended with 80 g of the adduct formed by reaction of SiCl$_4$, propylene oxide and glycidyl methacrylate in a mole ratio of 1:3:1 as described in Example 7 of copending application Ser. No. 347,264 to which 10 g of emulsifying agent (Emulsifier 221 from Sylvan Chemicals, which is an aryl polyoxyether) has been added.

The resulting silicon compound mixture is then blended with an RFL system to form the following impregnating composition:

| | Parts by weight solids |
|---|---|
| Silicon compound mixture (plus emulsifier) | 3.0 |
| Resorcinol-formaldehyde resin | 5.0 |
| Vinyl pyridine-butadiene-styrene terpolymer | 30.0 |

EXAMPLE 9

Using the procedure described in Example 10 of copending application Ser. No. 347,264, the adduct of SiCl$_4$, propylene oxide and epoxide ERR 4205 is prepared, and 90 g of the reaction product is blended with 20 g of emulsifying agent. The resulting mixture is then blended with 10 g of p-aminophenyltriethoxysilane which had been hydrolyzed with water.

The resulting mixture of silicon compounds is blended with an RFL system to form the following composition:

| | Parts by weight solids |
|---|---|
| Silicon compound mixture (plus emulsifier) | 1.5 |
| Resorcinol-formaldehyde resin | 4.0 |
| Natural rubber | 25.0 |

EXAMPLE 10

The adduct of 1 mole SiCl$_4$, 2 moles of propylene oxide and 1 mole of epoxide DER 332 described in Example 18 of Ser. No. 347,264 is mixed with hydrolyzed Z-6050. The resulting mixture of silicon compounds is formulated into the following composition of the type described in U.S. Pat. No. 3,424,608:

| | Parts by weight solids |
|---|---|
| Silicon compounds mixture (plus emulsifier) | 4 – 30 |
| Resorcinol-formaldehyde resin | 2 – 10 |
| Vinyl pyridine-butadiene-styrene terpolymer | 15 – 50 |
| Neoprene rubber | 25 – 50 |
| Polybutadiene | 5 –15 |

In a like manner, the compositions described in Examples 19 to 34 of copending application Ser. No. 347,264 can be employed in treating compositions of the type described in Examples 1 to 10 in lieu of the complex haloalkoxy compounds disclosed. Similarly, use can also be made of the beta-haloalkoxy groups described in copending application Ser. No. 347,241 as represented by the following examples.

EXAMPLE 11

Using the procedure described in Example 1 of the copending application Ser. No. 347,241, 1 mole of silicon tetrachloride is reacted with phenyl glycidyl ether and 1 mole of the diepoxide RD 2. 80 g of the raw reaction mixture is admixed with 20 g of gamma-aminopropyltriethoxy silane in 100 g of deionized water. The resulting mixture is then blended with the glass fiber treating composition of the type described in U.S. Pat. No. 3,567,671. The resulting composition contained the following:

| | Parts by weight |
|---|---|
| Silicon compound mixture | 150 |
| Resorcinol-formaldehyde resin (Penacolyte R2120 - 75% solids) | 48 |
| Vinyl pyridine-butadiene-styrene terpolymer (Gentac FS - General Tire and Rubber Co. 42% solids) | 9:0 |
| Vinyl chloride-vinylidene chloride copolymer (Dow latex 874 - 50% solids) | 350 |
| Microcrystalline paraffin wax (Vultex Wax no. 5 - 56% solids) | 200 |
| Water | 602 |

EXAMPLE 12

The raw reaction mixture described in Example 5 of copending application Ser. No. 347,241 is blended with an emulsifier and 15 grams of the polyamino functional silane Z-6050. The resulting composition is then blended with an impregnating composition of the type described above in Example 4, forming the following composition:

| | Parts by weight |
|---|---|
| Silicon compound mixture (plus emulsifier) | 115 |
| Resorcinol-formaldehyde resin (75% solids) | 48 |
| Vinyl pyridine-butadiene-styrene terpolymer (42% solids) | 900 |
| Dicarboxylated butadiene-styrene copolymer (50% solids - Pliolite 4121 from Goodyear Tire and Rubber Co.) | 350 |
| Microcrystalline paraffin wax (56% solids) | 200 |

| | Parts by weight |
|---|---|
| Water | 502 |

In like manner, each of the products of Examples 6 through 37 of copending application Ser. No. 347,241 can be employed in lieu of the beta-haloalkoxy silicon compounds exemplified in these two Examples.

As indicated, the compositions of Examples 1–12 can be employed in the treatment of individual glass fibers, forming a thin coating thereon, or the compositions can be applied as an impregnant to bundles of glass fibers which preferably have been previously sized with a glass fiber size composition. The resulting treated glass fibers or bundles of glass fibers can thereafter be combined directly with plastic resins in the manufacture of glass fiber reinforced plastics, laminates, coated fabrics and the like. It is generally preferred that the coated fibers be combined with plastic resins as described whereby the coating on the surfaces of the individual glass fiber filaments operates to securely anchor the glass fibers to the plastic resin. As used herein, the term "plastic resin" refers to and includes thermoplastic and thermosetting resins, such as polyesters, polyepoxides, polyamides, etc.

In the preferred use, glass fibers or bundles of glass fibers which have been treated in accordance with the present invention are employed as reinforcement for elastomeric materials in the manufacture of glass fiber-reinforced elastomeric products, such as rubber tires, drive belts, V-belts, etc. Regardless of whether bundles or individually coated glass fibers are employed, the composition of this invention serves to intertie the glass fibers with the elastomeric material to securely bond the glass fibers thereto.

In facilitating the combination of glass fibers treated in accordance with the present invention with elastomeric materials, the individually coated fibers or the impregnated bundles of glass fibers are mixed with an elastomeric material or otherwise laid down in the desired arrangement for combination with the elastomeric material as in the manufacture of glass fiber-reinforced elastomeric products. The resulting combination of glass fibers and elastomeric material is processed in a conventional manner by molding or curing under heat and compression for advancement of the elastomeric material to a cured or vulcanized stage while in combination with the treated glass fibers or bundles of glass fibers whereby the glass fibers or bundles of glass fibers become strongly integrated with the elastomeric material in the glass fiber-reinforced elastomeric product.

In the final system, the elastomeric material with which the glass fibers or bundles of glass fibers are combined, constitutes a continuous phase. Such continuous phase elastomeric materials may comprise elastomers or rubbers of the type incorporated into the treating compositions or the elastomeric material can differ therefrom. It is believed that the tie-in between the individually coated glass fibers or the impregnated bundles of glass fibers and the elastomeric materials forming the continuous phase occurs primarily during cure or vulcanization of the elastomeric material in combination with the treated glass fibers.

It will be apparent that various changes and modifications can be made in the details of procedure, formulation and use without departing from the spirit of the invention, especially as defined in the following claims.

I claim:

1. A composition for use in the treatment of glass fibers comprising (A) an aqueous dispersion having a solids content comprising 2 to 10 parts by weight of a resorcinol-aldehyde resin and 20 to 100 parts by weight of at least one elastomer and (B) from 0.1 to 25% of total solids of a combination of organo silicon compounds comprising (1) 1 to 30% by weight of an amino-substituted organo silane or its hydrolysis product and (2) 99 to 70% by weight of an organo silicon compound containing at least one beta-haloalkoxy group in the form of the reaction product of (a) a halosilane

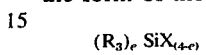

wherein $R_3$ is an organic group, X is halogen and $e$ is 0 or an integer from 1 to 2, (b) an alkylene oxide containing 1 to 6 carbon atoms and (c) an epoxide selected from the group consisting of a monoepoxide of the formula

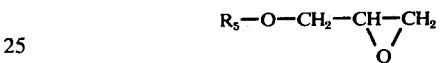

wherein $R_5$ is an aryl group substituted with an amino group, a halogen group, an alkyl group containing 1 to 20 carbon atoms and substituted derivatives thereof, an alkenyl group containing 2 to 8 carbon atoms, a

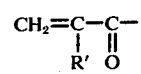

group wherein R' is hydrogen or methyl, a diepoxide of the formula

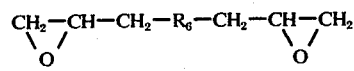

wherein $R_6$ is a divalent organic radical group and a cyclohexane diepoxide; with (b) and (c) being in the ratio of from 1 to 3 epoxide equivalents of (b) to from 0.5 to 3 epoxide equivalents of (c).

2. A composition as defined in claim 1 wherein the organo silane is a silane containing 1 to 3 readily hydrolyzable groups and containing at least one organic group attached directly to the silicon atom, with at least one of the organic groups being substituted by at least one amino group.

3. A composition as defined in claim 1 wherein the organo silane has the formula

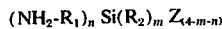

wherein $R_1$ is a divalent organic group selected from the group consisting of alkylene, alkenylene, cycloalkylene and arylene; $R_2$ is selected from the group consisting of alkyl, alkenyl, cycloalkyl, aryl and the hydroxy, epoxy or mercapto-substituted derivatives thereof; Z is a hydrolyzable group, $n$ is an integer from 1 to 3, $m$ is 0 or 1.

4. A composition as defined in claim 1 wherein the organo silane has the formula

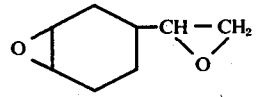

where *a* is an integer from 1 to 3, *b* is an integer from 1 to 3, *c* is an integer from 1 to 3, *d* is an integer from 1 to 2 and Z is a hydrolyzable group.

5. A composition as defined in claim 1 wherein the organo silane has the formula

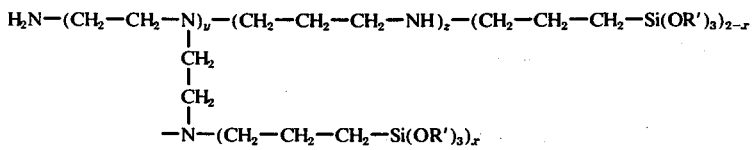

wherein R' is an alkyl group, *x* is 0 or an integer from 1 to 2 and *y* and *z* are integers.

6. A composition as defined in claim 1 wherein $R_5$ is selected from the group consisting of aryl, alkyl, alkenyl, substituted derivatives of the foregoing, acrylo and methacrylo.

7. A composition as defined in claim 1 wherein $R_6$ is selected from the group consisting of oxyalkyleneoxy, oxyalkyleneoxyalkyleneoxy, a group of the formula

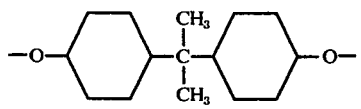

and a group of the formula

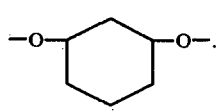

8. A composition as defined in claim 1 wherein the cyclohexane diepoxide is selected from the group consisting of compounds of the formula

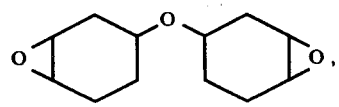

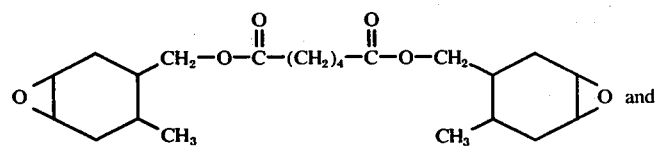

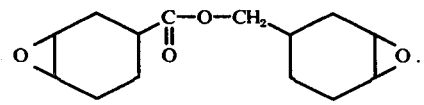

9. A composition as defined in claim 1 wherein the halosilane is a silicon tetrahalide.

10. A composition as defined in claim 1 wherein the reaction product contains 1 to 3 epoxide equivalents of (b) and 0.5 to 3.0 epoxide equivalents of (c) per mole of halosilane.

11. A composition as defined in claim 9 wherein (c) is selected from the group consisting of a compound of the formula

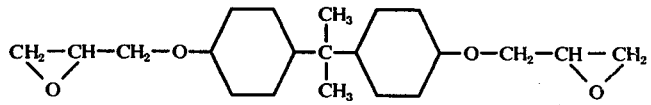

and a compound of the formula

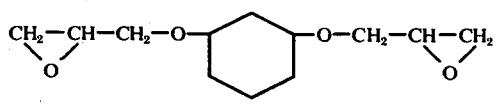

12. A composition as defined in claim 1 wherein the reaction product also includes a monohydric alcohol.

13. A composition as defined in claim 1 wherein the solids of the dispersion also contain a material selected from the group consisting of a vinyl chloride-vinylidene chloride copolymer, a microcrystalline paraffin wax, a carboxylated butadiene-styrene copolymer and mixtures thereof.

14. A composition as defined in claim 13 wherein the carboxylated copolymer is a dicarboxylated copolymer.

15. A composition for use in the treatment of glass fibers comprising (A) an aqueous dispersion having a solids content comprising 2 to 10 parts by weight of a resorcinol-aldehyde resin and 20 to 100 parts by weight of at least one elastomer and (B) from 0.1 to 25% of total solids of a combination of organo silicon compounds comprising (1) 1 to 30% by weight of an amino-substituted organo silane or its hydrolysis product and (2) 99 to 70% by weight of an organo silicon compound containing at least one beta-haloalkoxy group in the form of the reaction product of (a) a halosilane

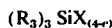

wherein $R_3$ is an organic group, X is halogen and $e$ is 0 or an integer from 1 to 2, (b) a monoepoxide selected from the group consisting of styrene oxide and a monoepoxide of the formula

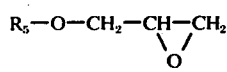

wherein $R_5$ is an aryl group substituted with an amino group, a halogen group, an alkyl group containing 1 to 20 carbon atoms and substituted derivatives thereof, an alkenyl group containing 2 to 8 carbon atoms, a

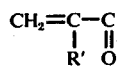

group wherein R' is hydrogen or methyl, and (c) at least one diepoxide selected from the group consisting of a diepoxide of the formula

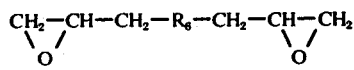

and a cyclohexane diepoxide with (b) and (c) being in the ratio of from 1 to 3 epoxide equivalents of (b) to 0.5 to 3 epoxide equivalents of (c).

16. A composition as defined in claim 15 wherein the reaction product contains 1 to 3 epoxide equivalents of (b) and 0.5 to 3.0 epoxide equivalents of (c) per mole of halosilane.

17. A composition as defined in claim 15 wherein a portion of (b) is replaced by an alkylene oxide or a monohydric alcohol.

18. A composition as defined in claim 15 wherein the solids of the dispersion also contain a material selected from the group consisting of a vinyl chloridevinylidene chloride copolymer, a microcrystalline paraffin wax, a carboxylated butadiene-styrene copolymer and mixtures thereof.

19. A composition as defined in claim 18 wherein the carboxylated copolymer is a dicarboxylated copolymer.

20. A composition for use in the treatment of glass fibers comprising (A) an aqueous dispersion having a solids content comprising 2 to 10 parts by weight of a resorcinol-aldehyde resin, 20 to 60 parts by weight of a vinyl pyridine-butadiene-styrene terpolymer, 15 to 40 parts by weight of a polymeric material selected from the group consisting of a vinyl chloride-vinylidene chloride copolymer and a carboxylated butadiene-styrene copolymer and 3 to 30 parts by weight of a microcrystalline paraffin wax, and (B) from 0.1 to 25% of total solids of a combination of organo silicon compounds comprising (1) 1 to 30% by weight of an amino-substituted organo silane or its hydrolysis product and (2) 99 to 70% by weight of an organo silicon compound containing at least one beta-haloalkoxy group in the form of the reaction product of (a) a halosilane

wherein $R_3$ is an organic group, X is halogen and $e$ is 0 or an integer from 1 to 2, (b) an alkylene oxide containing 1 to 6 carbon atoms and (c) an epoxide selected from the group consisting of an monoepoxide of the formula

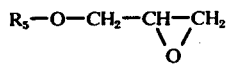

wherein $R_5$ is an aryl group substituted with an amino group, a halogen group, an alkyl group containing 1 to 20 carbon atoms and substituted derivatives thereof, an alkenyl group containing 2 to 8 carbon atoms, a

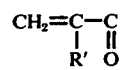

group wherein R' is hydrogen or methyl, a diepoxide of the formula

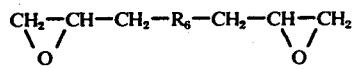

wherein $R_6$ is a divalent organic radical and a cyclohexane diepoxide; with (b) and (c) being in the ratio of from 1 to 3 epoxide equivalents of (b) to from 0.5 to 3 epoxide equivalents of (c).

21. A composition as defined in claim 20 wherein the halosilane is a tetrahalosilane.

22. A composition as defined in claim 20 wherein (c) is a diepoxide of the formula

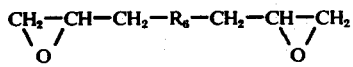

23. A composition as defined in claim 22 wherein (b) is propylene oxide.

24. A composition as defined in claim 20 wherein the polymeric material is a carboxylated butadiene-styrene copolymer.

25. A composition as defined in claim 24 wherein the carboxylated copolymer is a dicarboxylated butadiene-styrene copolymer.

26. A composition as defined in claim 22 wherein $R_6$ is selected from the group consisting of a group of the formula

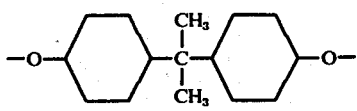

and a group of the formula

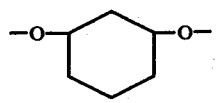

* * * * *